(12) United States Patent
Atieh et al.

(10) Patent No.: US 8,865,019 B2
(45) Date of Patent: Oct. 21, 2014

(54) METHOD OF INHIBITING FREE RADICAL POLYMERIZATION OF STYRENE

(75) Inventors: Muataz Ali Atieh, Dhahran (SA); Adnan Al-Amer, Dhahran (SA); Issam Thaher Amr, Dhahran (SA)

(73) Assignees: King Fahd University of Petroleum and Minerals, Dhahran (SA); King Abdulaziz City for Science and Technology, Riyadh (SA)

( * ) Notice: Subject to any disclaimer, the term of this patent is extended or adjusted under 35 U.S.C. 154(b) by 802 days.

(21) Appl. No.: 13/100,009

(22) Filed: May 3, 2011

(65) Prior Publication Data

US 2012/0280174 A1   Nov. 8, 2012

(51) Int. Cl.
| | |
|---|---|
| C09K 3/00 | (2006.01) |
| C09K 15/00 | (2006.01) |
| C08F 2/38 | (2006.01) |
| B82Y 30/00 | (2011.01) |
| C07C 7/20 | (2006.01) |
| C08F 12/08 | (2006.01) |

(52) U.S. Cl.
CPC . *C07C 7/20* (2013.01); *B82Y 30/00* (2013.01); *C08F 12/08* (2013.01); *Y10S 977/748* (2013.01); *Y10S 977/752* (2013.01)
USPC ...... 252/182.12; 252/397; 977/748; 977/752; 526/82

(58) Field of Classification Search
CPC .............. C08K 3/00; C08K 3/04; C08F 2/40; C08F 12/08; C07C 7/20; C01B 31/022; C01B 2202/06; B82Y 30/00; B82Y 40/00
USPC ...................... 252/182.12, 397; 977/748, 752
See application file for complete search history.

(56) References Cited

U.S. PATENT DOCUMENTS

| | | | |
|---|---|---|---|
| 4,237,326 A | 12/1980 | Fuga et al. | |
| 4,929,778 A | 5/1990 | Roling | |
| 5,302,681 A | 4/1994 | McClain | |
| 5,420,371 A | 5/1995 | Malhotra et al. | |
| 5,605,992 A | 2/1997 | Urashima et al. | |
| 6,331,262 B1 | 12/2001 | Haddon et al. | |

FOREIGN PATENT DOCUMENTS

| | | |
|---|---|---|
| JP | 2008222939 A | 9/2008 |
| WO | WO/90/12072 | 10/1990 |
| WO | WO 02085974 A1 * | 10/2002 |

OTHER PUBLICATIONS

Loutfy et al. Commercial Production of Fullerenes and Carbon Nanotubes. Perspectives of Fullerene Nanotech. 2002. pp. 35-46.*
Kramer, Carl. Fullerene Research Advantages. Nova Publishers. 2007, pp. 244-245.*
Sanjiv Mehrotra, Asutosh Nigam and Ripudaman Malhotra, "Effect of [60]fullerene on the radical polymerization of alkenes", *Chem. Commun.*, 1997 463.

* cited by examiner

*Primary Examiner* — Harold Pyon
*Assistant Examiner* — Tanisha Diggs
(74) *Attorney, Agent, or Firm* — Richard C Litman

(57) ABSTRACT

The method of inhibiting free radical polymerization of styrene includes adding multi-walled carbon nanotubes are added to the styrene monomer. The addition of the multi-walled carbon nanotubes at a concentration of 5% by weight is found to provide effective inhibition of the polymerization of the styrene. Greater decreases in the conversion rate of styrene to polystyrene are found through the addition of multi-walled carbon nanotubes functionalized with a carboxylic group (COOH). Still greater decreases in the conversion rate of styrene to polystyrene are found through the addition of multi-walled carbon nanotubes functionalized with octadecylamine ($C_{18}H_{39}N$). The multi-walled carbon nanotubes may also be functionalized with other functional groups, such as octadecanoate, polyethylene glycol or phenol. The functionalized multi-walled carbon nanotubes only require addition at a concentration of 1% by weight to be effective in polymerization inhibition.

3 Claims, 2 Drawing Sheets

METHOD OF INHIBITING FREE RADICAL POLYMERIZATION OF STYRENE

BACKGROUND OF THE INVENTION

1. Field of the Invention

The present invention relates to the prevention of unwanted polymerization of monomers during storage, shipment, and manufacturing processes, and particularly to a method of inhibiting free radical polymerization of styrene.

2. Description of the Related Art

Styrene is a vinyl monomer. Various conditions may induce the formation of free radicals in styrene, thereby initiating chain polymerization. Typically, in the handling and storage of styrene monomer, the styrene temperature must be carefully controlled at around 10° C. to prevent styrene polymerization. In order to ensure purity, polymerization inhibitors are typically added to styrene monomers that are to be stored or shipped. In relatively hot climates, and during the transportation of the styrene, the initial inhibitor level is usually increased to avoid autocatalytic polymerization, which becomes self-sustaining above 20° C. Similarly, certain manufacturing processes that utilize styrene monomer may include processing the styrene at temperatures that induce the formation of radicals and unwanted chain growth polymerization of the styrene.

The inhibition of polymerization in styrene with carbonaceous nanomaterials is known, e.g., by p-tert-butylcatechol or by hydroquinone. However, the more of an inhibitor that is added to the styrene, the less pure the styrene becomes, and thus requires complicated filtration and purification processes before the styrene monomer can be used. A highly effective polymerization inhibitor requiring a minimal amount to be added to the styrene would be desirable.

Thus, a method of inhibiting free radical polymerization of styrene solving the aforementioned problems is desired.

SUMMARY OF THE INVENTION

In order to prevent the conversion of styrene monomers into polystyrene, a quantity of multi-walled carbon nanotubes are added to the styrene. The addition of the multi-walled carbon nanotubes at a concentration of 5% by weight is found to provide effective inhibition of the polymerization of the styrene. Greater decreases in the conversion rate of styrene to polystyrene are found through the addition of multi-walled carbon nanotubes functionalized with a carboxylic group (COOH). Still greater decreases in the conversion rate of styrene to polystyrene are found through the addition of multi-walled carbon nanotubes functionalized with octadecylamine ($C_{18}H_{39}N$). The multi-walled carbon nanotubes may also be functionalized with other functional groups, such as octadecanoate, polyethylene glycol or phenol. The functionalized multi-walled carbon nanotubes only require addition at a concentration of 1% by weight to be effective in polymerization inhibition.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
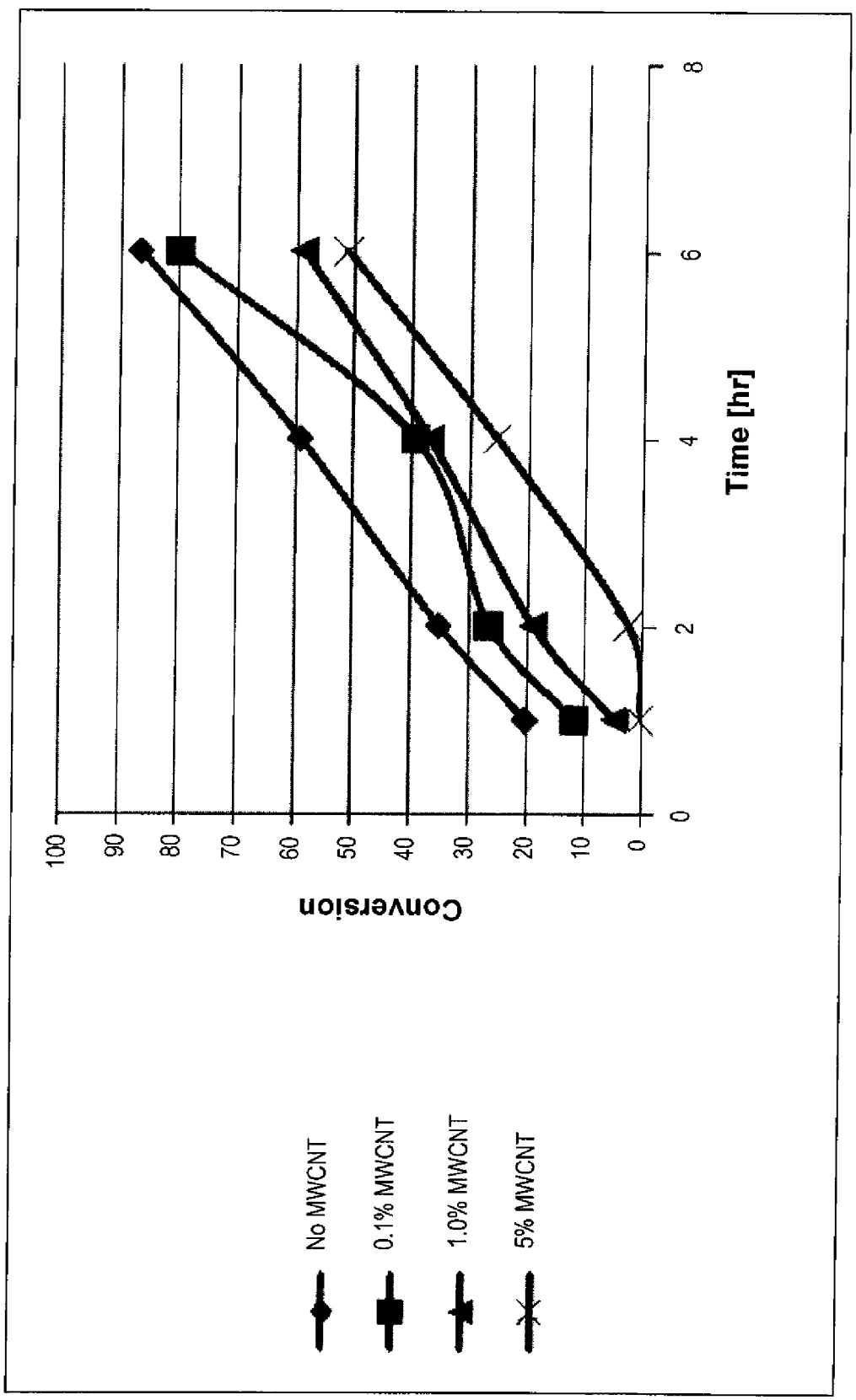
FIG. 1 is a graph comparing conversion rates of styrene monomer to polystyrene through the addition of 0.1%, 1.0% and 5.0% by weight multi-walled carbon nanotubes at 115° C.

As will be shown below, in order to prevent the conversion of styrene monomers into polystyrene, a quantity of multi-walled carbon nanotubes are added to the styrene. The addition of the multi-walled carbon nanotubes at a concentration of 5% by weight is found to provide effective inhibition of the polymerization of the styrene. Greater decreases in the conversion rate of styrene to polystyrene are found through the addition of multi-walled carbon nanotubes functionalized with a carboxylic group (COOH). Further, still greater decreases in the conversion rate of styrene to polystyrene are found through the addition of multi-walled carbon nanotubes functionalized with octadecylamine ($C_{18}H_{39}N$). The multi-walled carbon nanotubes may also be functionalized with other functional groups, such as octadecanoate, polyethylene glycol or phenol. The functionalized multi-walled carbon nanotubes only require addition at a concentration of 1% by weight to be effective in polymerization inhibition.

Occasionally, a distinction is made in the literature between a polymerization "retardant", which slows down polymer formation but cannot stop it completely, and a polymerization "inhibitor", which completely prevents polymer formation. As used herein, the term "inhibiting" or "inhibit" refers to either slowing down or reducing the rate of polymer formation, or to completely preventing polymer formation, except as explicitly noted to the contrary.

Styrene monomer was obtained from Sigma-Aldrich® and was washed and distilled to remove any added inhibitor before use. Multi-walled carbon nanotubes (MWCNTs) with nanotube diameter of 8-15 nm, length of 10-50 μM, specific area of 230 $m^2/g$ and purity of greater than 95% were purchased from Nanostructured & Amorphous Material, Inc. to be used as the polymerization inhibitor.

In order to modify the MWCNTs, a 1:10 ratio of MWCNTs to concentrated nitric acid was mixed in a round-bottomed flask and refluxed at 130° C. for 48 hours with continuous stirring in order to functionalize the surface of the carbon nanotubes with a carboxylic functional group (COOH). Upon cooling, the mixture was carefully washed with deionized water to remove any remaining traces of un-reacted acid until the pH value was 7 (signifying zero acidity). The acid-modified MWCNTs (hereafter referred to as MWCNT-COOH) were then filtered and dried at 80° C.

A fixed amount of MWCNT-COOH was further functionalized with octadecylamine by adding a few drops of sulfuric acid at a MWCNT-COOH to octadecylamine ratio of 1:10 at the octadecylamine melting temperature of 55° C. The mixture was stirred for six hours to yield amine-modified MWCNTs (hereafter referred to as MWCNT-Amine). Any remaining traces of un-reacted sulfuric acid and octadecylamine were removed via repeated washing with deionized water and toluene, respectively.

In order to study polymerization, quantities of MWCNTs, MWCNT-Amine, and MWCNT-COOH were placed in round-bottom flasks that were sealed with rubber septums and purged with nitrogen through repeated vacuum/nitrogen cycles. After the last cycle, the flasks were purged with nitrogen for ten minutes. To ensure no oxygen flowed into the flasks, 10 ml of the monomer (styrene) was injected using a syringe with a transfer needle. The flasks were immersed in an oil bath that was kept at the reaction temperature (115° C.) for a fixed polymerization time. After the polymerization time passed, the flasks were removed from the oil bath and the reaction mixtures were diluted with THF. Then, methanol was added to precipitate the formed polymer, which was recovered by filtration, followed by drying at 70° C.

Three different weight percentages of MWCNTs (0.1, 1.0 and 5.0 wt %) were mixed with fixed amounts of styrene monomer (10 ml) in each round bottom flask. The polymerization temperature was fixed at 115° C., while polymerization time was varied from between one and six hours. The conversion of styrene monomer both with and without added MWCNTs was calculated using the following equation:

$$\% \text{ conversion} = \left(\frac{w_{rp}}{w_i}\right) \times 100\%,$$

where $w_{rp}$ represents the weight of recovered polystyrene and $w_i$ represents the initial weight of the styrene monomer.

FIG. 1 shows the conversion rates of styrene monomer to polystyrene at different polymerization times. By increasing the polymerization time, the degree of polymerization increases. FIG. 1 clearly shows that the addition of MWCNTs reduces the polymerization rate. For example, after one hour of polymerization, the conversion of the pure styrene (without MWCNTs) to polystyrene reaches 20%, while by adding small amount of MWCNTs, such as 0.1 wt %, the conversion was reduced by 50% and became only 10%.

Further increases in the amount of MWCNTs leads to reduction of the conversion rate of styrene significantly. At 5 wt % of MWCNTs in styrene, and after one hour of polymerization time, the styrene remains as a monomer and there was no polymerization, which indicates that the MWCNTs inhibit the reaction and stop any polymerization. After six hours of polymerization time, the conversion rates of styrene without addition of MWCNTs reaches up to ~90%, while by adding MWCNTs at 0.1, 1 and 5 wt %, the conversion rates were 80.1%, 58.9% and 51.4%, respectively, and all were less than the conversion of pure styrene without MWCNTs. This is due to the fact that MWCNTs have electron affinities similar to those of fullerenes, and therefore behave as radical traps in chain reactions, such as polymerization.

Figure 2:
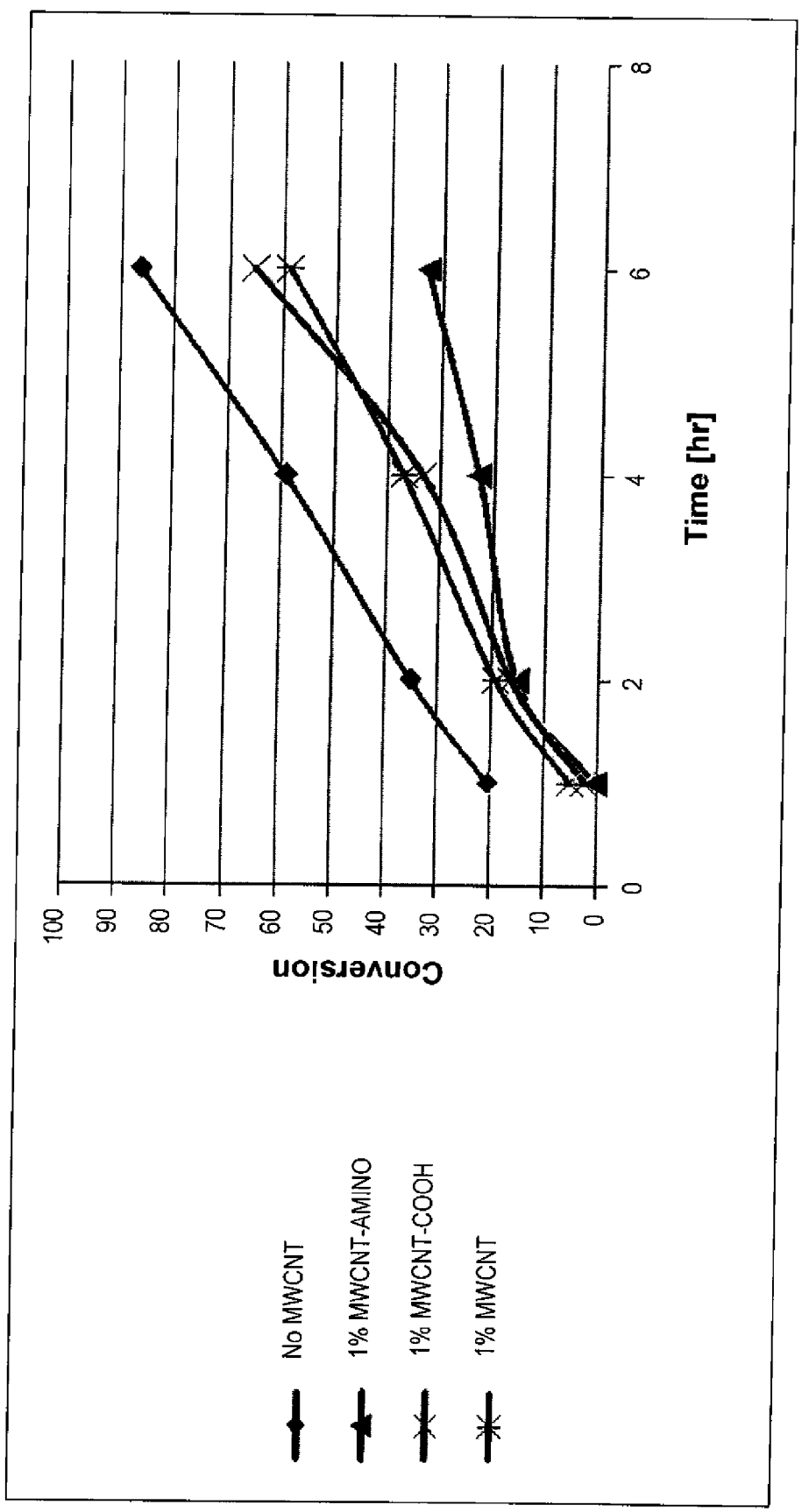
FIG. 2 is a graph comparing conversion rates of styrene monomer to polystyrene through the addition of 1.0% by weight multi-walled carbon nanotubes, multi-walled carbon nanotubes functionalized with a carboxylic group, and multi-walled carbon nanotubes functionalized with octadecylamine at 115° C.

As shown in FIG. 2, significant reduction in the conversion of styrene monomer to polystyrene was achieved when the added MWCNTs were functionalized with different functional groups, such as the amine and carboxylic groups. No significant polymerization was found to occur after one hour of polymerization time when MWCNT-Amine or MWCNT-COOH was added with only 1 wt %, which indicates that the functional group on the surface of the MWCNTs plays a major role in the sharp reduction of the conversion. After six hours, the conversion rate did not rise above 34% for the amine functional group, and did not rise above 65% for the carboxylic functional group, thus showing the high efficiency of modified MWCNTs with functional groups in inhibiting the polymerization of styrene.

Thus, non-modified MWCNTs and modified MWCNTs, particularly MWCNT-Amine and MWCNT-COOH, are found to show a clear reduction in the conversion rate of styrene monomer to polystyrene at high temperatures (115° C.), and with different polymerization times from between one and six hours.

It is to be understood that the present invention is not limited to the embodiments described above, but encompasses any and all embodiments within the scope of the following claims.

We claim:

1. A method of inhibiting free radical polymerization of styrene, comprising the step of adding a quantity of functionalized multi-walled carbon nanotubes to styrene sufficient to inhibit polymerization thereof, wherein the multi-walled carbon nanotubes are functionalized with a functional group selected from the group consisting of octadecanoate, polyethylene glycol, and phenol.

2. The method of inhibiting free radical polymerization of styrene as recited in claim 1, wherein the functionalized multi-walled carbon nanotubes are added to the styrene at a concentration of approximately 1% by weight.

3. A method of inhibiting free radical polymerization of styrene, comprising the step of adding an inhibitor to styrene monomers in a quantity sufficient to inhibit free radical polymerization of the styrene monomers, the inhibitor comprising multi-walled carbon nanotubes, wherein the multi-walled carbon nanotubes are functionalized with a functional group selected from the group consisting of octadecanoate, polyethylene glycol, and phenol.

* * * * *